(12) United States Patent
Sauer

(10) Patent No.: US 11,633,215 B2
(45) Date of Patent: Apr. 25, 2023

(54) NEEDLE ASSEMBLY FOR PLEURAL SPACE INSUFFLATION AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 107 days.

(21) Appl. No.: 16/197,524

(22) Filed: Nov. 21, 2018

(65) Prior Publication Data

US 2019/0083131 A1 Mar. 21, 2019

Related U.S. Application Data

(62) Division of application No. 15/731,093, filed on Apr. 17, 2017, now Pat. No. 10,179,008.

(Continued)

(51) Int. Cl.
*A61B 17/34* (2006.01)
*A61B 17/00* (2006.01)
(Continued)

(52) U.S. Cl.
CPC .... *A61B 17/3474* (2013.01); *A61B 17/00234* (2013.01); *A61B 17/3403* (2013.01); *A61B 17/3417* (2013.01); *A61M 13/003* (2013.01); *A61B 17/3496* (2013.01); *A61B 2017/00243* (2013.01); *A61B 2017/00809* (2013.01); *A61B 2017/306* (2013.01); *A61B 2017/3413* (2013.01); *A61M 2202/0225* (2013.01); *A61M 2202/0468* (2013.01); *A61M 2210/101* (2013.01)

(58) Field of Classification Search
CPC ........ A61M 5/42; A61M 5/425; A61M 13/00; A61M 13/003; A61M 13/006; A61M 2210/101; A61M 5/3291; A61B 17/00234; A61B 17/3403; A61B 17/3417; A61B 17/3474; A61B 17/3496; A61B 2017/306
See application file for complete search history.

(56) References Cited

U.S. PATENT DOCUMENTS 2,728,341 A * 12/1955 Roehrzbislaw ......... A61M 5/28
D24/114
3,540,112 A * 11/1970 Knox .................. A61M 5/3286
72/370.1

(Continued)

OTHER PUBLICATIONS

Jun. 5, 2018 Office Action; U.S. Appl. No. 15/731,093.

*Primary Examiner* — Kami A Bosworth
(74) *Attorney, Agent, or Firm* — Michael E. Coyne; Christopher B. Miller

(57) ABSTRACT

A needle assembly for pleural space insufflation is disclosed. The needle assembly has an outer shaft defining one or more pliable tissue receivers. The needle assembly also has a needle moveable within the outer shaft from a retracted position to an engaged position that does not extend past a distal end of the outer shaft. A method of pleural space insufflation is also disclosed. A parietal pleura is contacted with a distal end of an outer shaft that defines one or more pliable tissue receivers. The distal end of the outer shaft is pushed against the parietal pleura so that a portion of the parietal pleura enters the one or more pliable tissue receivers. A needle is advanced within the outer shaft so that the needle pierces the parietal pleura.

14 Claims, 6 Drawing Sheets

Related U.S. Application Data

(60) Provisional application No. 62/324,751, filed on Apr. 19, 2016.

(51) Int. Cl.
*A61M 13/00* (2006.01)
*A61B 17/30* (2006.01)

(56) References Cited

U.S. PATENT DOCUMENTS

| | | | | |
|---|---|---|---|---|
| 5,071,412 A * | 12/1991 | Noda | | A61M 5/007 |
| | | | | 604/176 |
| 5,374,250 A * | 12/1994 | Dixon | | A61B 5/153 |
| | | | | 604/110 |
| 5,588,432 A * | 12/1996 | Crowley | | A61B 5/6848 |
| | | | | 600/374 |
| 6,471,688 B1 * | 10/2002 | Harper | | A61M 5/145 |
| | | | | 424/424 |
| 6,592,552 B1 * | 7/2003 | Schmidt | | A61B 17/3478 |
| | | | | 604/164.01 |
| 6,733,479 B1 | 5/2004 | Ott | | |
| 8,758,299 B2 * | 6/2014 | Sadowski | | A61M 5/3134 |
| | | | | 604/115 |
| 10,646,662 B2 * | 5/2020 | Sadowski | | A61M 5/425 |
| 2005/0165366 A1 * | 7/2005 | Brustad | | A61M 25/0043 |
| | | | | 604/264 |
| 2007/0112325 A1 | 5/2007 | Wieselthaler | | |
| 2008/0312611 A1 * | 12/2008 | Racz | | A61M 25/0009 |
| | | | | 604/272 |
| 2011/0166509 A1 | 7/2011 | Gross | | |
| 2013/0006189 A1 * | 1/2013 | Tsais | | A61M 5/46 |
| | | | | 604/192 |
| 2016/0331910 A1 * | 11/2016 | Imai | | A61M 5/3293 |

* cited by examiner

NEEDLE ASSEMBLY FOR PLEURAL SPACE INSUFFLATION AND METHODS THEREOF

RELATED APPLICATIONS

This application is a divisional application of U.S. Pat. No. 10,179,008 issued on Jan. 15, 2019 and entitled "NEEDLE ASSEMBLY FOR PLEURAL SPACE INSUFFLATION AND METHODS THEREOF". The U.S. Pat. No. 10,179,008 Patent claims priority to U.S. Provisional Patent Application No. 62/324,751 filed on Apr. 19, 2016 and entitled, "NEEDLE ASSEMBLY FOR PLEURAL SPACE INSUFFLATION." Therefore, this application claims priority to both the U.S. Pat. No. 10,179,008 Patent and 62/324,751 application. The U.S. Pat. No. 10,179,008 Patent and 62/324,751 application are also hereby incorporated by reference in their entirety.

FIELD

The claimed invention relates to surgical devices, and more specifically to a needle assembly for pleural space insufflation.

BACKGROUND

Minimally invasive surgical techniques continue to evolve for the benefit of patients. In the past, many cardiac surgical procedures were performed using a sternotomy (opening or cracking of the sternum in the chest) to gain access to the heart and often had recovery times which were measured in months, with multiple weeks of post-operative care in the hospital, substantial amounts of post-operative pain, and long-lasting restrictions which kept patients away from favorite activities and work. By contrast, many of these same cardiac procedures, such as aortic and/or mitral valve repair/replacement, may be done using minimally invasive surgery (MIS) techniques. With MIS, the surgeons perform all the steps of the operation through one or more small incisions in a patient, for example, a small incision in the intercostal spaces between a patient's ribs. A variety of MIS tools and viewing scopes have been developed to facilitate working through such small access sites. While the intercostal openings may provide adequate access to pertinent portions of a patient's heart, in some patients the heart may be positioned further away from the chosen incision than is ideal, thereby making the MIS cardiac procedure more difficult and potentially time consuming. Therefore, there is a need for MIS devices and methods which enable surgeons to move or gently nudge the heart closer to the intercostal incision through which the heart will be accessed for a given procedure. In addition to reducing the cost of surgical procedures, such devices and methods can reduce the amount of time patients need to be attached to a cardiopulmonary bypass (CPB) machine, thereby reducing the likelihood of CPB-related side effects. Faster and more reliable cardiac operations offer additional benefits, such as reduced surgical team fatigue and more efficient use of critical resources. Expediting cardiac surgery can also improve patient outcomes.

SUMMARY

A needle assembly for pleural space insufflation is disclosed. The needle assembly has an outer shaft defining one or more pliable tissue receivers. The needle assembly also has a needle moveable within the outer shaft from a retracted position to an engaged position that does not extend past a distal end of the outer shaft.

A method of pleural space insufflation is also disclosed. A parietal pleura is contacted with a distal end of an outer shaft that defines one or more pliable tissue receivers. The distal end of the outer shaft is pushed against the parietal pleura so that a portion of the parietal pleura enters the one or more pliable tissue receivers. A needle is advanced within the outer shaft so that the needle pierces the parietal pleura.

DETAILED DESCRIPTION

Figure 1:
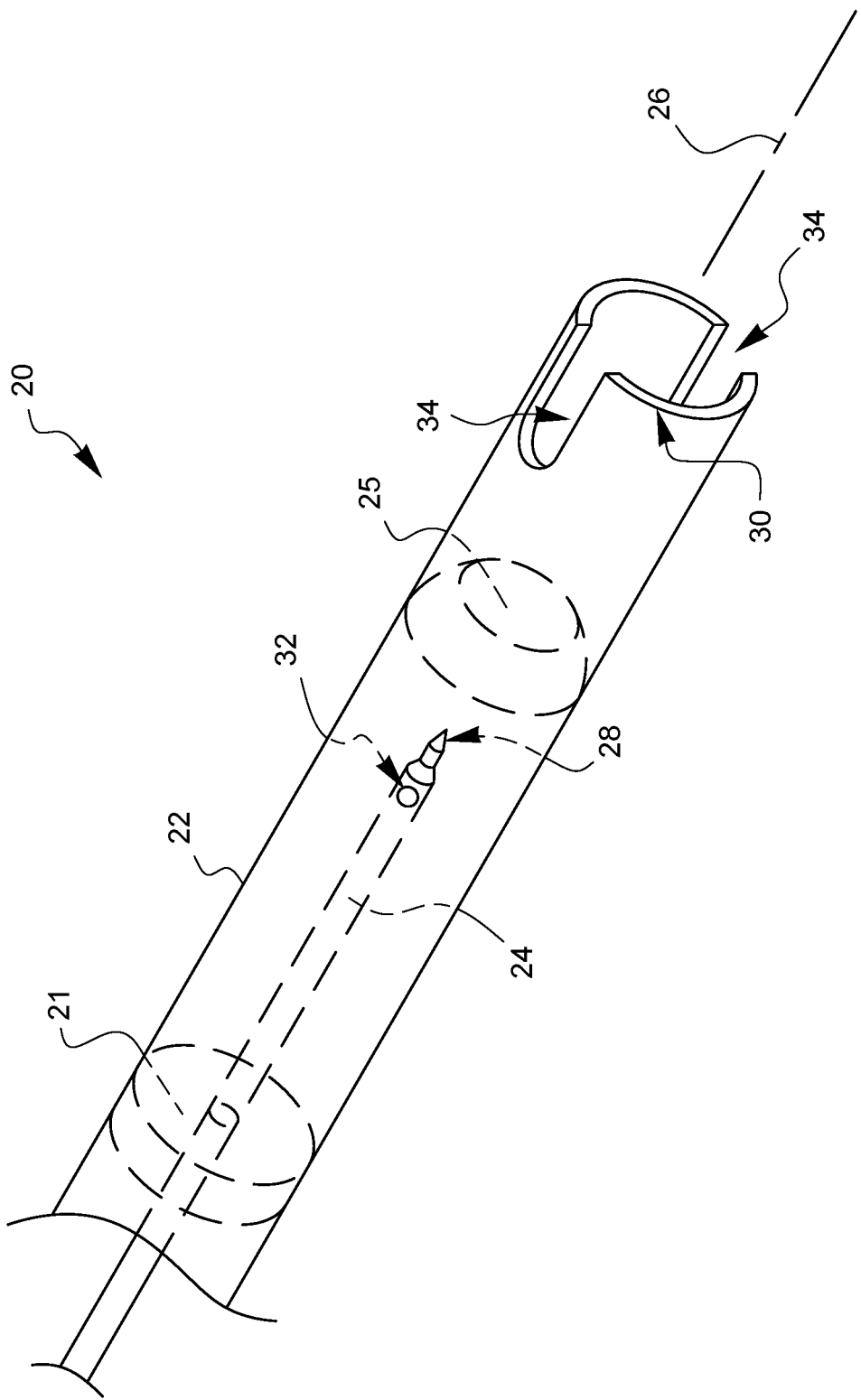
FIG. 1 is a perspective view of one embodiment of a needle assembly for pleural space insufflation.

The human respiratory system is responsible for taking in oxygen from the atmosphere and expelling carbon-dioxide. The main organs of the respiratory system are the lungs. Each of the lungs is covered by a membrane which folds back on itself to form a two-layered membranous pleural sac. The portion of the membrane which covers the lungs is known as the visceral pleura, while the outer portion of the membrane is called the parietal pleura. The parietal pleura is attached to the diaphragm muscle in the abdomen and to the ribs. The area between the visceral pleura and the parietal pleura is known as the pleural space. Each of the left and right pleural spaces (corresponding to the left and right lungs, respectively) is normally filled with a fluid that 1) helps the visceral pleura and parietal pleura slide relative to each other and 2) helps to hydrostatically couple the visceral pleura to the parietal pleura.

Respiration includes two distinct phases: inspiration and expiration. Under normal respiratory conditions, during inspiration, the diaphragm muscle is flexed downward while the rib muscles pull upward on the ribs. This pulls on the pleural and visceral membranes, creating a negative pressure within the lungs relative to an ambient atmosphere. This negative pressure causes air to enter the airways of the mouth and/or nasal passages, flow down the trachea, and pass into the bronchi and alveoli of the lungs, causing the lungs to expand at the same time. While the air is in the alveoli, oxygen is exchanged for carbon dioxide in the blood which is being pumped through the lungs by the heart. During expiration, the diaphragm and rib muscles relax, causing the thoracic cavity to return to a smaller size, thereby removing the negative pressure which had drawn and held the air in the lungs. The lung tissue, and in particular, the alveoli, which had been stretched like balloons by the incoming air during inspiration, now return to a resting state during expiration as they expel the air held therein following the removal of the negative pressure.

Normally, it is desirable to maintain the patency of the pleural space so that the lungs are able to draw air within as described above. Injuries such as stab wounds which pierce the parietal pleura or both the parietal pleura and the visceral pleura allow air to enter the pleural space from one or more undesirable paths, thereby breaking the ability of the chest cavity to create a negative pressure around the lung during inspiration. Such an injury can cause a lung to collapse, thereby complicating breathing for a patient.

At certain times, however, it may be desirable (or has been desirable in the medical field) to collapse a lung on purpose. As an example, in 1932, Janos Veress developed a tool, now called the Veress needle, which was used to collapse an infected lung of a tuberculosis patient in order to allow lesions in the lung to heal. The Veress needle is a spring-loaded needle with an outer sharp cannula and a dull inner stylet through which air may pass. When mechanical pressure is not applied to the Veress needle, the inner (rounded or dull) stylet protrudes from the end of the outer, sharp cannula, thereby preventing the sharp portion from causing inadvertent damage to tissue. When pressure is applied to the needle, however, the inner stylet is pushed back into the outer cannula, allowing the sharp outer cannula to puncture tissue. As soon as the sharp portion of the cannula clears the tissue it is penetrating, however, the inner stylet is pushed back out by a spring to protect other tissue from the sharp cannula. Veress used this needle to puncture the thoracic cavity while reducing the likelihood that the sharp outer cannula could puncture the visceral pleura. Unfortunately, in many places around the lungs, the pleural space between the parietal pleura and visceral pleura is so small that there may not be room for the dull inner stylet to push forward before the sharp outer cannula is already cutting through the visceral pleura. From the point of view of desiring to collapse a lung, this may not matter initially, but this may make it more difficult to reinflate the lung later.

Figure 5:
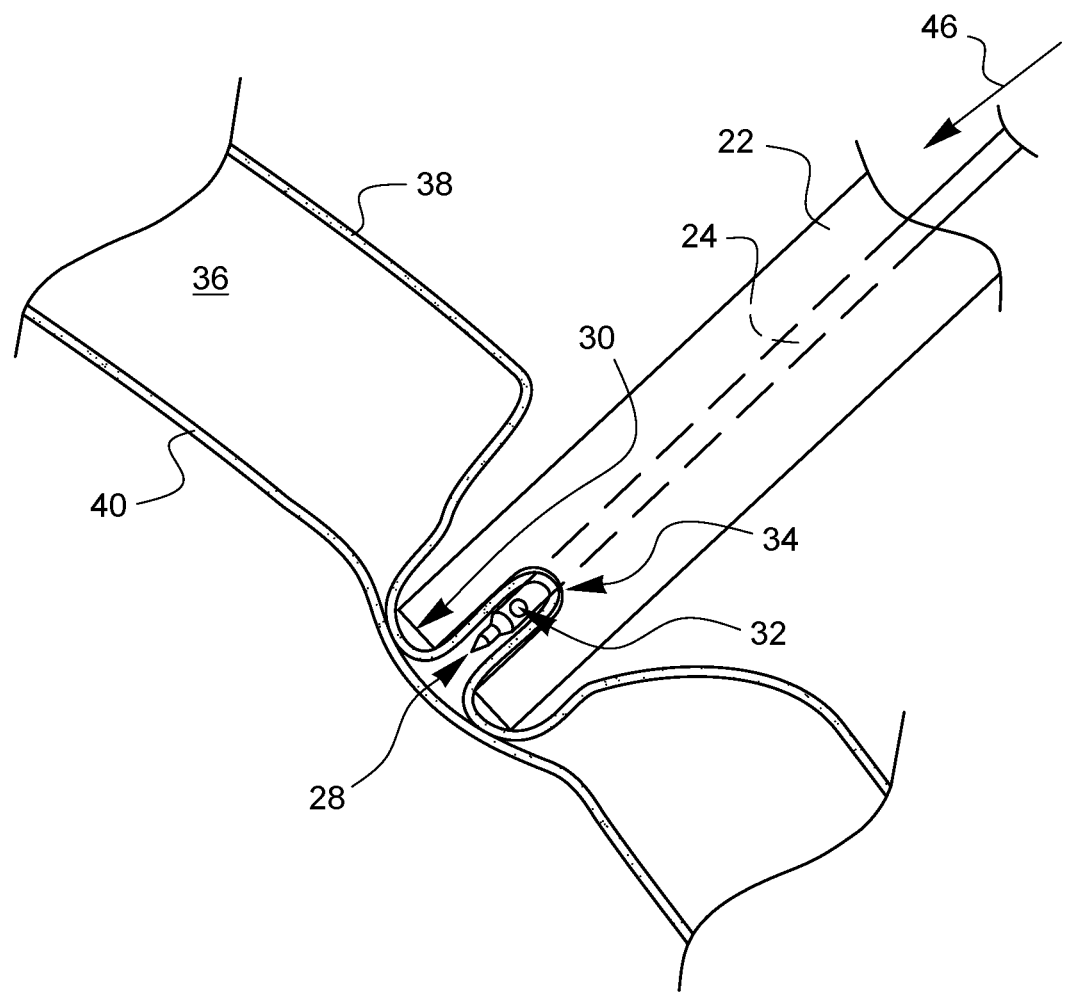
FIG. 5 schematically illustrates the needle assembly of FIG. 1 when the needle has been actuated to pierce the parietal pleura held in the pliable tissue receiver of the needle assembly without being able to pierce the visceral pleura.

FIG. 1 illustrates one embodiment of a needle assembly 20 for pleural space insufflation. It should be noted that the drawings herein are not necessarily drawn to scale. The needle assembly 20 has an outer shaft 22 and a needle 24 which is movable parallel to a longitudinal axis 26 of the shaft 22 within the shaft 22. The needle 24 is preferably actuatable between a resting position where the needle tip 28 is farther away from the distal end 30 of the outer shaft 22 (such as shown in FIG. 1) and a piercing position where the needle tip 28 is closer to the distal end 30 (such as shown in FIG. 5). Ideally, but not necessarily, the needle tip 28 does not extend past the distal end 30 of the outer shaft 22. As shown in FIG. 1, the needle 24 may define one or more fluid communication holes 32 near the needle tip 28. The one or more fluid communication holes 32 provide access to one or more channels (not shown) passing within the needle 24. These channels within the needle may simply be vented to atmosphere, or they may be coupled or coupleable to one or more fluid sources that can be opened up, activated, or otherwise turned on to push fluid through the fluid communication hole 32 in the needle 24. Some non-limiting examples of suitable fluids include air, carbon-dioxide, humified carbon-dioxide, water, plasma, synthetic or natural pleural fluid, and saline solution. In addition to being connectable to such pressurized or pressurizable fluid sources, the fluid communication hole 32 may also be coupled to a vacuum source to allow fluid (air and/or gas) to be withdrawn through the fluid communication hole 32. Those skilled in the art are well aware of structures to provide fluid channels within a needle as well as how to couple fluid sources and/or a vacuum source to those fluid channels.

The needle assembly 20 may also include one or more needle guides 21 within the shaft 22 to help maintain a position of the needle 24 as it slides within the shaft 22. One or more of such needle guides may provide a fluid seal to prevent fluid from passing in a proximal direction through the outer shaft. Other embodiments may have one or more fluid seals 25 which are not needle guides. The fluid seal 25 may be a material which the needle 24 can penetrate, but which is compliant and will form a closure around the needle 24 after it has passed through the seal 25. Still other embodiments may size the needle 24 relative to the shaft 22 so that the inner wall of the shaft is the needle guide. For ease of explanation, other figures will not show embodiments of a needle guide 21 or a fluid seal 25, however it should be understood that these features could be present.

The outer shaft 22 also defines one or more pliable-tissue receivers 34 which extend proximally from the distal end 30 of the shaft 22. The distal end 30 of the shaft 22 is preferably blunted so that it does not act as a sharp surface.

Figure 2:
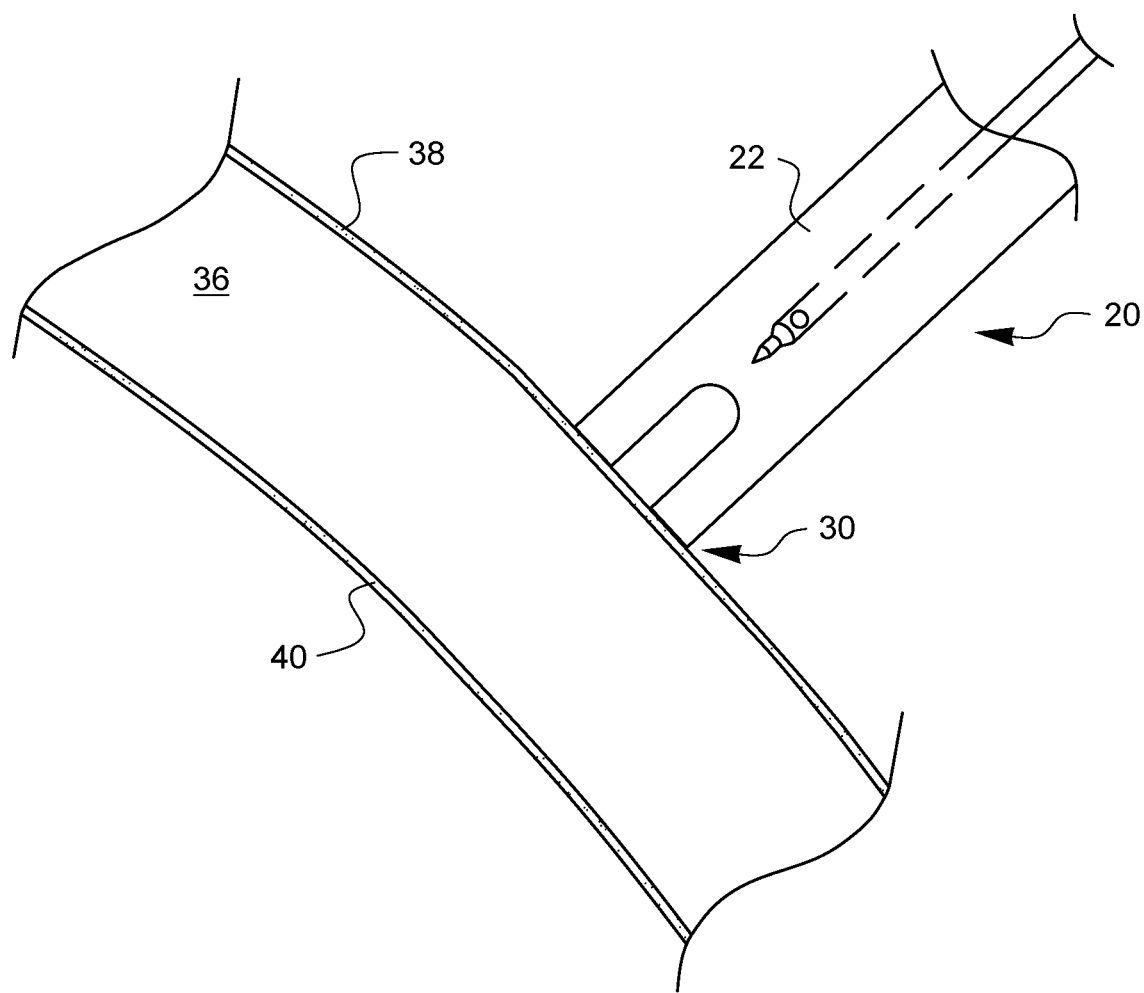
FIG. 2 schematically illustrates the needle assembly of FIG. 1 as being placed against the parietal pleura (an outer surface of a membrane which covers a lung).

FIG. 2 schematically illustrates a pleural space 36 bounded by a parietal pleura 38 on a chest side and a visceral pleura 40 on a lung side. The needle assembly 20 has been given access to the parietal pleura 38 (for example, through a MIS opening) and the distal end 30 of the outer shaft 22 has been placed against the parietal pleura 38.

Figure 3:
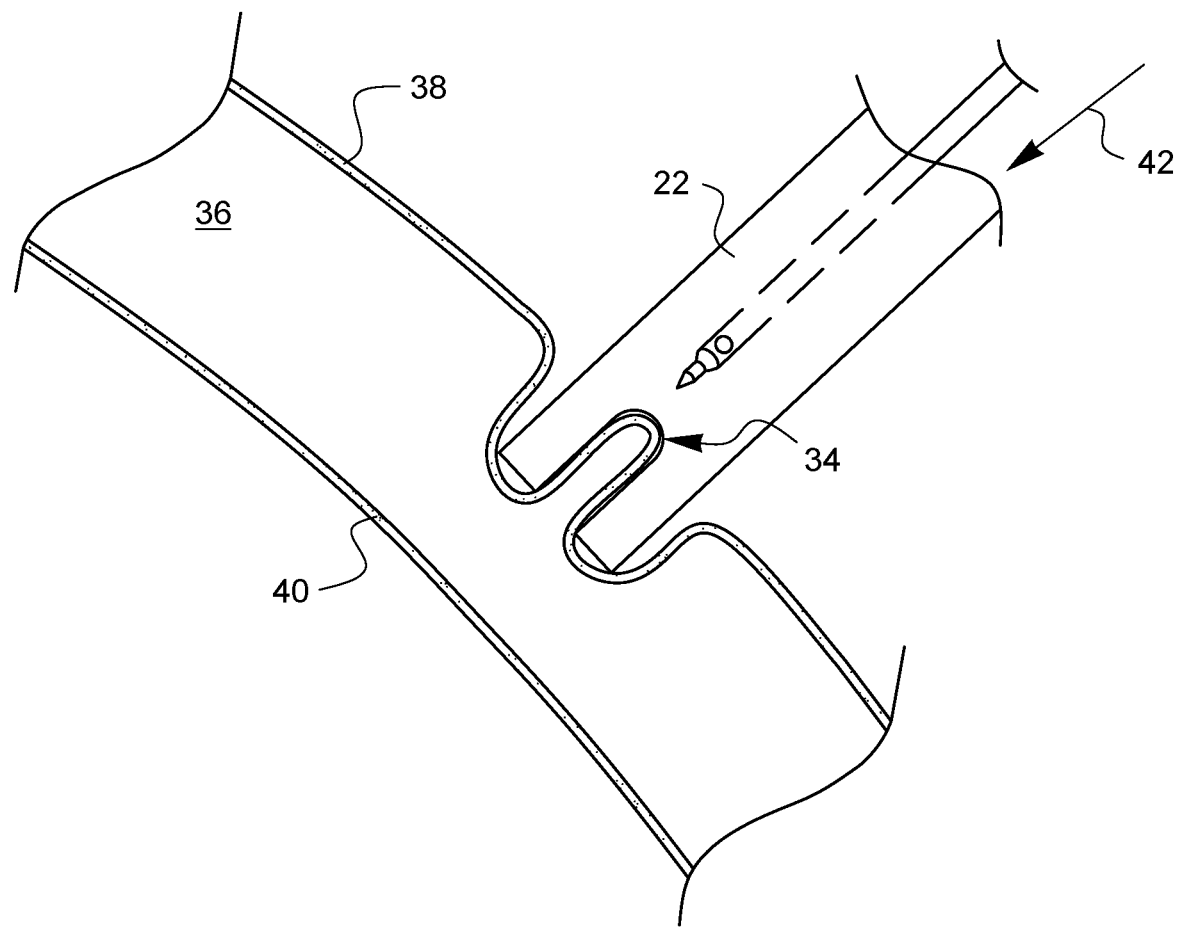
FIG. 3 schematically illustrates the needle assembly of FIG. 1 when starting to be pushed against the parietal pleura of a lung.

As shown in FIG. 3, pressure is applied 42 to the outer shaft 22 so that it pushes against the parietal pleura 38. Since the parietal pleura 38 is fluid-backed, it is relatively pliable and tends to be drawn into the pliable tissue receivers 34 of the outer shaft 22.

Figure 4:
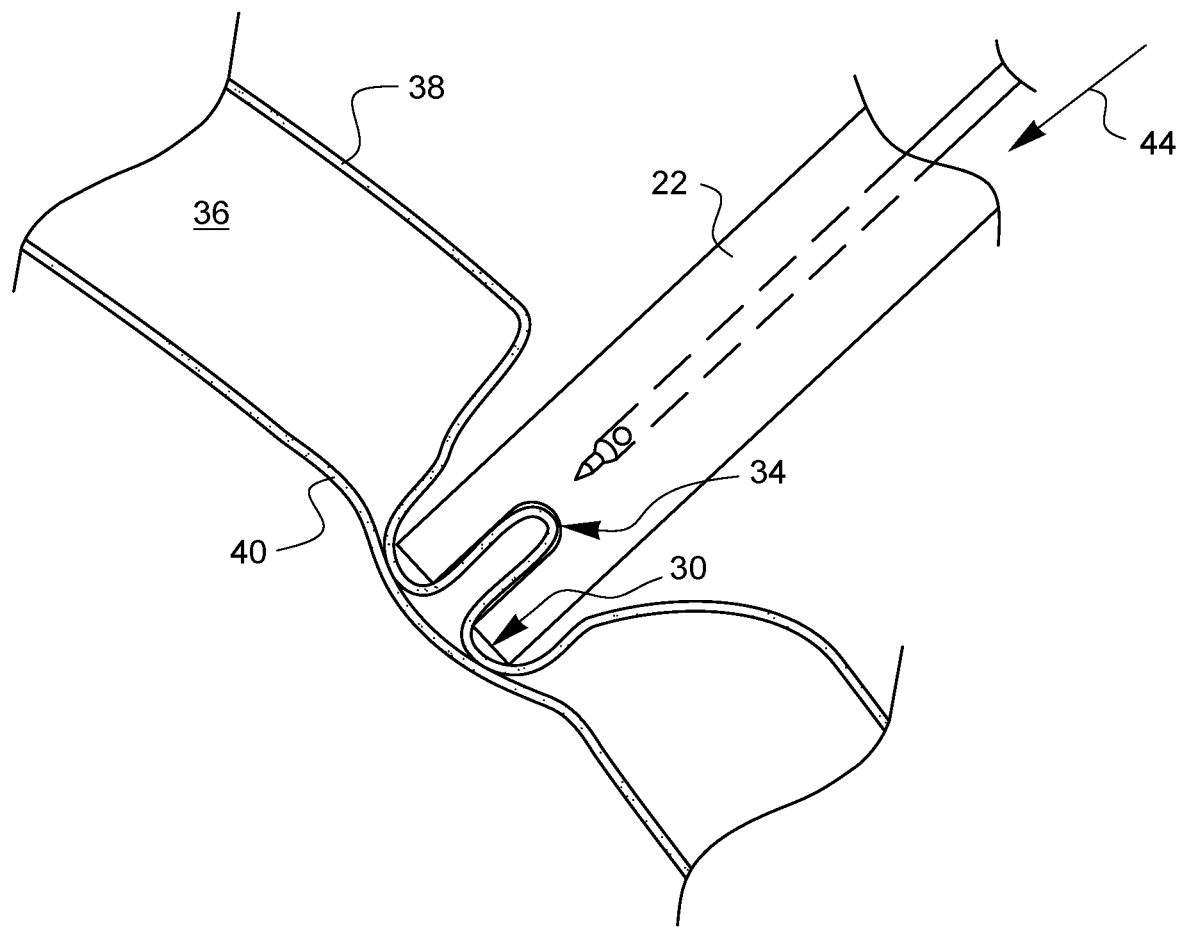
FIG. 4 schematically illustrates the needle assembly of FIG. 1 when pushed further against the parietal pleura of a lung, creating a known differential position of the parietal pleura (the outer surface of the membrane covering the lung) relative to the visceral pleura (the inner surface of the membrane covering the lung).

As shown in FIG. 4, if further pressure 44 is applied, the distal end 30 of the outer shaft 22 may start to push on the visceral pleura 40 through the parietal pleura 38. However, since the visceral pleura 40 is supported by the underlying lung tissue, it is not as pliable as the parietal pleura 38. As such, the visceral pleura 40 tends not to be drawn into the pliable tissue receiver 34, and, instead, tends to be stretched over the distal end 30. This creates a known differential position of the parietal pleura 38 held within the pliable tissue receiver 34 and the visceral pleura 40 held outside the distal end 30. As illustrated in FIG. 5, such a differential position can be exploited so that the inner needle 24 can pierce only the parietal pleura 38.

As shown in FIG. 5, the needle 24 has been actuated in a distal direction 46 such that it pierces the parietal pleura 38 held in the pliable tissue receiver 34. Since the needle tip 28 does not extend past the distal tip 30 of the outer shaft 22, the needle tip 28 does not pierce the visceral pleura 40. This offers a much lower risk of iatrogenic perforation of the visceral pleura and a lower risk of lung parenchymal tissue trauma. The fluid communication hole 32 is open to the pleural space 36 after piercing the parietal pleura 38, thereby providing a passageway for an insufflating pressure into the pleural space. Such an insufflating pressure could be created by the introduction of one or more fluids (liquid or gas) through the fluid communication hole 32.

One non-limiting, advantageous use of the needle assembly 20 is that it may enable a surgeon to insufflate the pleural space surrounding the left lung during a cardiac surgical procedure. The insufflated left pleural space may gently displace the contents of the mediastinum (including the heart) to the right, and more particularly towards a minimally invasive surgical access point made through a right intercostal space in the ribs for the purpose of an aortic and/or a mitral valve repair/replacement. The ability to position the heart advantageously using a minimally invasive technique can reduce surgical time thereby improving patient outcomes and reducing surgical team fatigue.

Figure 6:
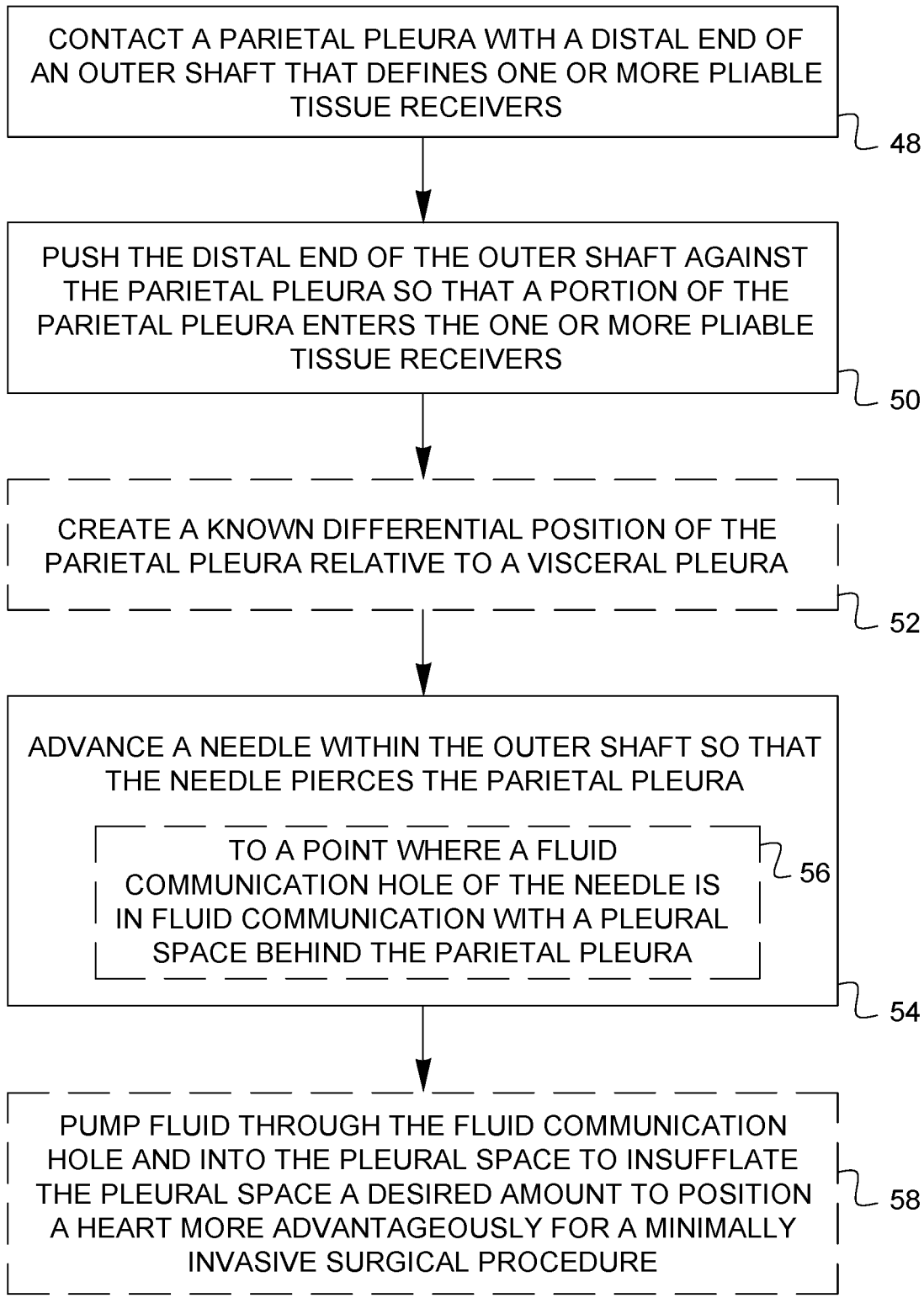
FIG. 6 illustrates one embodiment of a method of pleural space insufflation.

FIG. 6 illustrates a method of pleural space insufflation. A parietal pleura is contacted 48 with a distal end of an outer shaft that defines one or more pliable tissue receivers. The distal end of the outer shaft is pushed 50 against the parietal pleura so that a portion of the parietal pleura enters the one or more pliable tissue receivers. As described above, the outer shaft may optionally be pushed against the backside of the less pliable visceral pleura to create 52 a known differential position of the parietal pleura relative to the visceral pleura. A needle is then advanced 54 within the outer shaft so that the needle pierces the parietal pleura. As described above, this may be done without piercing the visceral pleura because the needle does not advance past the distal end of the outer shaft. Optionally, the needle may be advanced 56 to a point where a fluid communication hole of the needle is in fluid communication with a pleural space behind the parietal pleura. Optionally, fluid may be pumped 58 through the fluid communication hole and into the pleural space to insufflate the pleural space a desired amount to position a heart more advantageously for a minimally invasive surgical procedure.

Various advantages of a needle assembly for pleural space insufflation and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As just one example, the shaft may be hemostatic and may be configured to affix to intercostal muscle and potentially to skin. The shaft can be offered in a variety of lengths, depending on a patient's body habitus. The shaft may also be constructed of a radiopaque material or an ultrasound-viewable material so that the device can show up on one or more types of imaging equipment for aiding in placement of the needle assembly. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A needle assembly for pleural space insufflation, comprising:
   an outer shaft extending along a longitudinal axis from a proximal end to a distal end, wherein the outer shaft is at least partially defined by at least one outer surface defining an exterior portion of the outer shaft and at least one interior surface defining an interior portion of the outer shaft, the interior portion of the outer shaft extending to the distal end of the outer shaft such that the distal end of the outer shaft is open, wherein one or more pliable tissue receiver slots are defined in the outer shaft, and each of the one or more pliable tissue receiver slots extends from a distal end at the distal end of the outer shaft to a proximal end at an intermediate point between the proximal end of the outer shaft and the distal end of the outer shaft, each of the one or more pliable tissue receiver slots extending along a respective slot longitudinal axis that is parallel to the longitudinal axis of the outer shaft, and each of the one or more pliable tissue receiver slots being at least partially defined by respective first and second lateral edges that each extend parallel to and laterally offset from the respective slot longitudinal axis and at least partially defined by a respective semi-circular top edge that extends from a proximal end of the respective first lateral edge to a proximal end of the respective second lateral edge, and wherein for each of the one or more pliable tissue receiver slots, a length distance from the respective proximal end of the pliable tissue receiver slot to the respective distal end of the pliable tissue receiver slot is greater than a width distance between the respective first and second lateral edges, and wherein the at least one outer surface defining the exterior portion of the outer shaft is a semi-cylindrical surface that extends at least from the intermediate point to the distal end of each of the one or more pliable tissue receiver slots;
   one or more needle guides disposed within the interior portion of the outer shaft;
   a fluid seal in the outer shaft, the fluid seal disposed proximal to the one or more pliable tissue receiver slots, wherein the fluid seal is not displaceable relative to the outer shaft; and
   a needle that extends along a needle axis from a proximal end to a distal end, wherein the needle is displaceable along the needle axis between a retracted position and an engaged position, the needle comprising:
      a needle tip disposed at the distal end of the needle;
      one or more channels disposed within an interior portion of the needle; and
      a fluid communication hole formed in a portion of the needle proximal to the needle tip, the fluid communication hole being in fluid communication with at least one of the one or more channels disposed within the interior portion of the needle,
      wherein in the retracted position, the needle tip is disposed within the interior portion of the outer shaft a first distance from the distal end of the outer shaft, and in the engaged position, the needle tip is disposed within the interior portion of the outer shaft a second distance from the distal end of the outer shaft, wherein the first distance is greater than the second distance, and
      wherein when the needle is in the engaged position, the needle tip is disposed (a) proximal to the distal end of each of the one or more pliable tissue receiver slots and (b) distal to the proximal end of each of the one or more pliable tissue receiver slots-such that the needle tip is configured to penetrate a portion of tissue that is disposed within at least one portion of the one or more pliable tissue receiver slots.

2. The needle assembly of claim 1, wherein the outer shaft comprises a material which is viewable by ultrasound.

3. The needle assembly of claim 1, wherein the outer shaft comprises a radiopaque material.

4. The needle assembly of claim 1, wherein the needle axis is coaxially aligned with the longitudinal axis of the outer shaft.

5. The needle assembly of claim 1, wherein the one or more pliable tissue receiver slots include a first pliable tissue receiver slot and a second pliable tissue receiver slot defined in the outer shaft, and the first pliable tissue receiver slot and the second pliable tissue receiver slot are symmetrically formed about the longitudinal axis of the outer shaft.

6. The needle assembly of claim 1, wherein the fluid communication hole extends through a lateral surface of the needle proximal to the needle tip.

7. The needle assembly of claim 6, wherein a second fluid communication hole is formed in a second portion of the needle proximal to the needle tip, the second fluid communication hole being in fluid communication with the one or more channels disposed within the interior portion of the needle.

8. The needle assembly of claim 1, wherein the at least one interior surface defining the interior portion of the outer shaft has a cross-sectional shape of a first circle having a first diameter, and wherein a lateral surface of the needle has a cross-sectional shape of a second circle having a second diameter that is less than the first diameter.

9. The needle assembly of claim 8, wherein the second diameter is dimensioned such that one or more portions of the lateral surface of the needle contact the at least one interior surface defining the interior portion of the outer shaft such that the at least one interior surface defining the interior portion of the outer shaft is the one or more needle guides.

10. The needle assembly of claim 8, wherein the lateral surface of the needle extends proximally from a first needle point proximal to the needle tip to a second needle point at or distal to the proximal end of the needle.

11. The needle assembly of claim 1, wherein when the needle is in the engaged position, a proximal portion of the needle is configured to be coupled to a vacuum source such that the one or more channels allow fluid to be withdrawn through the fluid communication hole from an area adjacent to the fluid communication hole.

12. The needle assembly of claim 1, wherein when the needle is in the engaged position, a proximal portion of the needle is configured to be coupled to a fluid source such that the one or more channels allow fluid from the fluid source to be supplied through the fluid communication hole to an area adjacent to the fluid communication hole.

13. The needle assembly of claim 1, wherein an annular surface extends between the at least one outer surface of the outer shaft and the at least one interior surface of the outer shaft at the distal end of the outer shaft such that no sharp surfaces are disposed at the distal end of the outer shaft.

14. The needle assembly of claim 1, wherein when the needle is in the engaged position, the fluid communication hole is disposed distal to the point between the proximal end of the outer shaft and the distal end of the outer shaft such that the fluid communication hole is configured to be distal to the portion of tissue that is disposed within the at least one portion of the one or more pliable tissue receiver slots.

* * * * *